United States Patent [19]
Jinotti

[11] Patent Number: 5,242,084
[45] Date of Patent: Sep. 7, 1993

[54] FLUID DISPENSING APPARATUS

[76] Inventor: Walter J. Jinotti, 10 Scott St., New Brunswick, N.J. 08903

[21] Appl. No.: 888,024

[22] Filed: May 26, 1992

[51] Int. Cl.⁵ .............................................. B65D 35/30
[52] U.S. Cl. .................................... 222/103; 222/340; 222/386
[58] Field of Search ................................ 222/92–107, 222/213, 340, 386

[56] References Cited

U.S. PATENT DOCUMENTS 3,847,304  11/1974  Cohen ................................... 222/105
3,902,635  9/1975  Jinotti ................................... 222/103

Primary Examiner—Jesus D. Sotelo
Attorney, Agent, or Firm—Robert A. Green

[57] ABSTRACT

Fluid dispensing apparatus comprising a housing containing two box-like members, an upper and a lower with the lower box being adapted to slide into the upper box to provide a space beneath it for receiving a plastic bag containing a fluid to be fed therefrom. A drive plate is disposed within and in operative relation with the lower box and a plurality of springs disposed between the drive plate and the lower box cause the lower box to apply pressure to the plastic bag to dispense fluid therefrom.

13 Claims, 6 Drawing Sheets

FLUID DISPENSING APPARATUS

BACKGROUND OF THE INVENTION

U.S. Pat. No. 3,902,635 of Walter J. Jinotti describes and claims apparatus for dispensing fluid, particularly blood. The apparatus described in this patent operates satisfactorily and has been in use for many years. However, the invention described herein provides improvements in the structure and operation of the apparatus described in the aforementioned patent.

SUMMARY OF THE INVENTION

The apparatus of the invention comprises a housing including an area for receiving a blood bag and a piston drive mechanism for applying pressure to the blood bag to dispense blood therefrom. The apparatus includes a novel spring arrangement for applying pressure to the piston mechanism.

DESCRIPTION OF THE INVENTION

Figure 1:
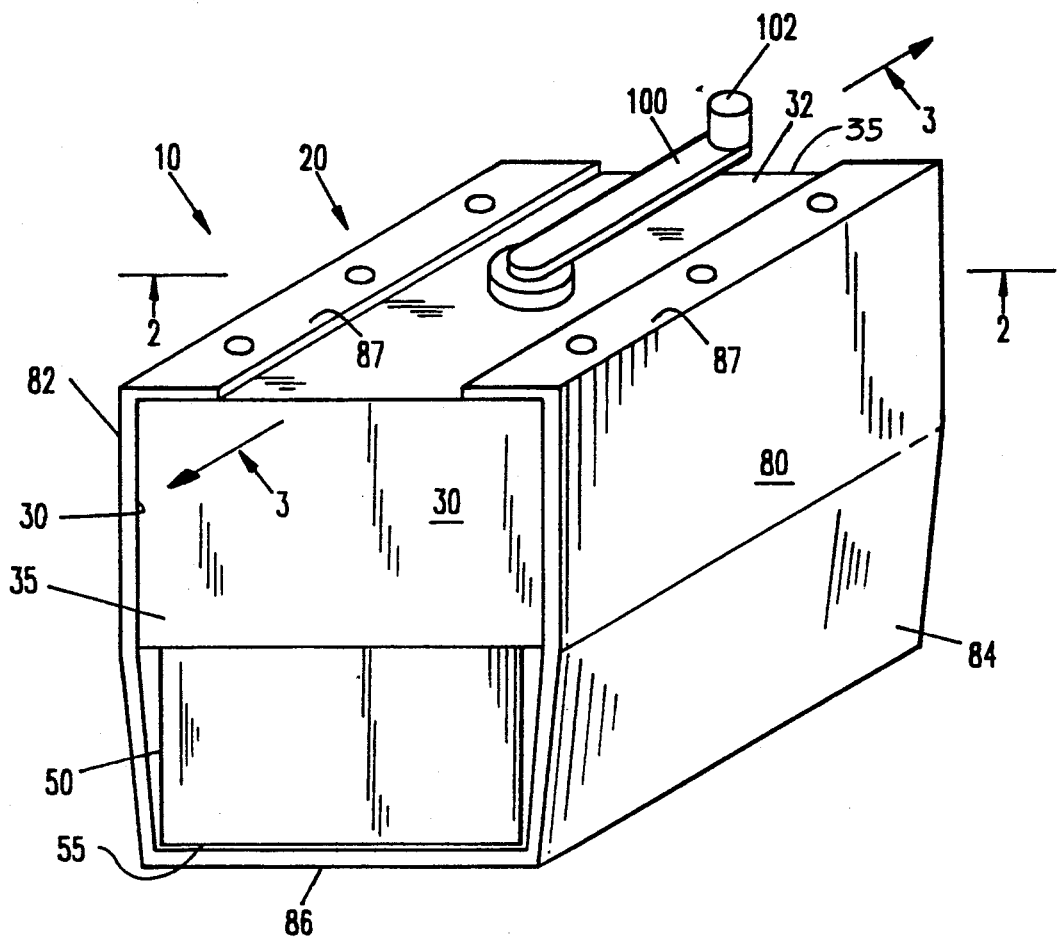
FIG. 1 is a perspective view of apparatus embodying the invention.
Figure 2:
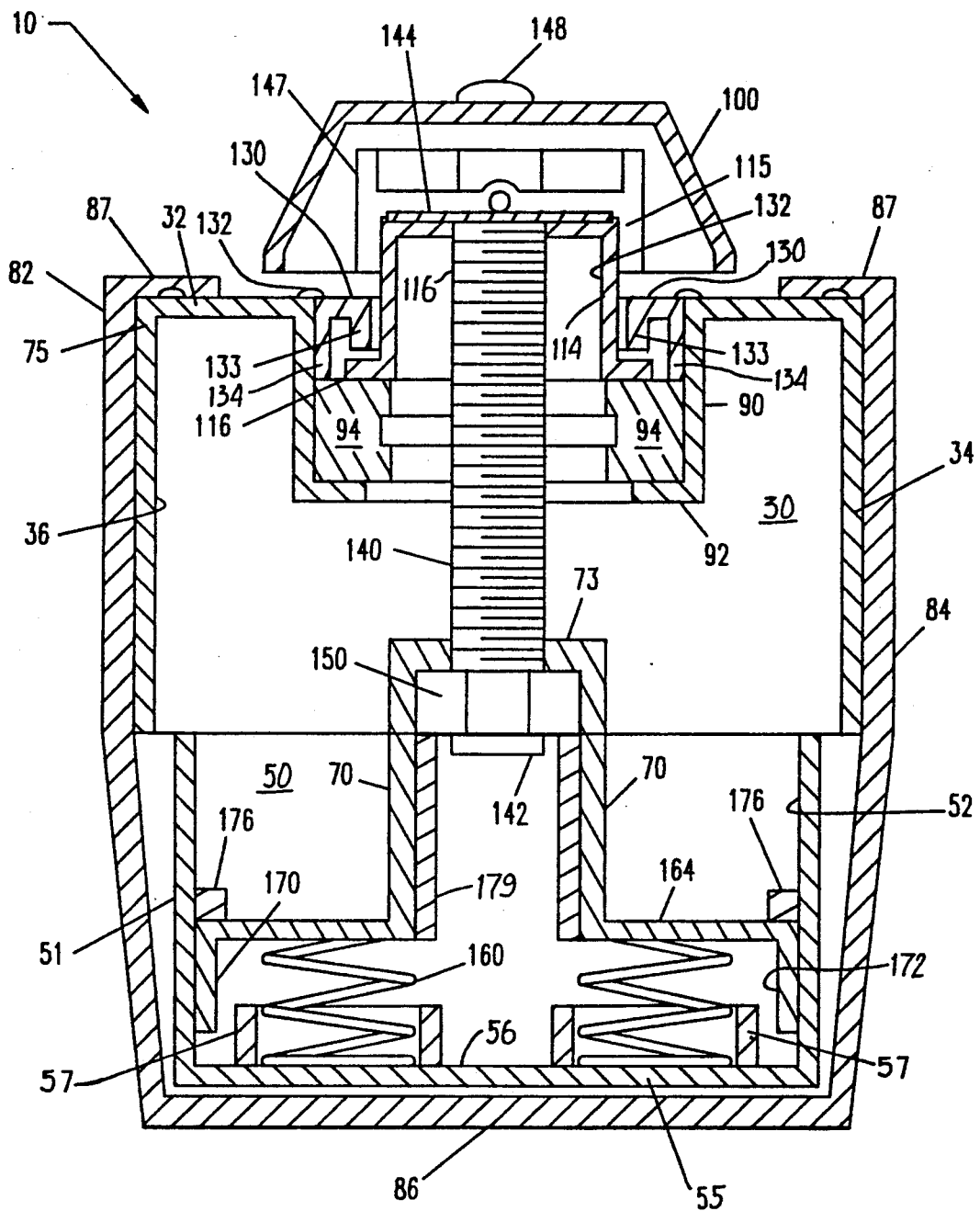
FIG. 2 is a sectional view along the lines 2—2 in FIG. 1.

Apparatus embodying the invention is useful for dispensing any type of fluid held in a deformable container, but it is especially useful for dispensing blood from a blood bag and this use is described herein.

Blood dispensing apparatus 10, which may be made of metal, plastic or the like, comprises a housing 20 which includes a first generally U-shaped upper box-like member 30 which has a top wall 32, end walls 33 and 35, side walls 34 and 36 but no bottom wall. The box member 30 faces down with its open end down. If desired, the apparatus 10 includes a handle or hanger 38 secured to the upper box member 30 and including a frame 40 having a handle 42 pivotably secured thereto.

The housing 20 also includes a second lower open-ended box-like member 50 which has its open end facing up, and is generally of the same shape as box member 30 but somewhat smaller so that it can slide into the open lower end of box 30. The second box 50 has side walls 51 and 52, end walls 53 and 54 and a bottom wall 55 but no top wall and is thus open at the top. The inner surface 56 of the bottom wall 55 of the second box 50 is provided with at least two short annular tubes 57 in which springs 58 are retained.

The housing also includes a wrap-around enclosure wall member 80 which encloses the first and second box member 30 and 50, overlaying the side walls and the bottom wall thereof. The enclosure 80 has side walls 82 and 84 and a bottom wall 86 and a top wall made up of two spaced apart strips 87 which are welded or otherwise secured to the top wall 32 of the upper box 30. The strips 87 are spaced apart to make room for a handle to be described.

At about the center of the top wall 32 of the first box 30 a cylindrical sleeeve 90 extends downwardly a suitable distance into the inside of the apparatus 10 and it terminates in an annular lip 92. A bearing 94 is seated inside the sleeve 90 and rests on the lip 92. A rotatable handle 100 having a swivel knob 102 at its end is secured to a threaded shaft or screw 140 which is disposed inside the sleeve 90.

The handle assembly includes an annular sleeve or hub 114 which is seated on bearing 94 by means of an annular foot 116 formed at its lower end. The hub 114 is held in place by a generally U-shaped annular member 130 which is suitably secured inside sleeve 90 at the upper end thereof. The annular member 130 includes one arm 133 which is positioned close to the foot 116 of hub 114 and a second annular arm 134 which is seated on bearing 94 and holds the bearing securely in place.

Figure 3:
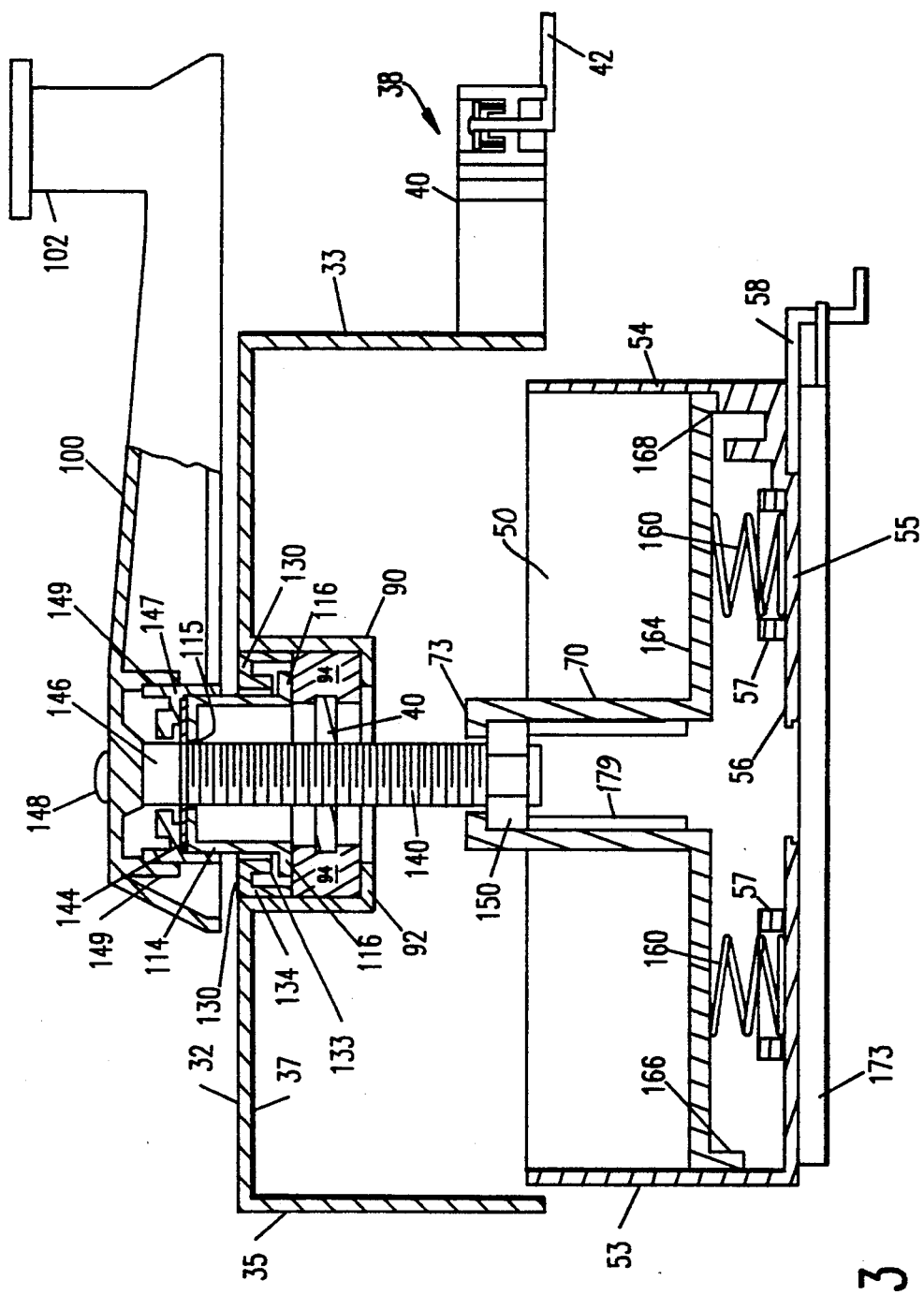
FIG. 3 is a sectional view along the lines 3—3 in FIG. 1.

A hexagonal nut 150 is threaded on the lower end 142 of screw 140. The shaft 140 carries an annular ring or disk 144 which is seated on the top surface of a hub 114 which surrounds the upper end of the screw 140. An annular sleeve 147 is seated on the disk 144 and hub 114 and the handle 100 is secured to the upper end 146 of screw 140 by a screw or bolt 148. The handle 100 carries ribs 149 which engage sleeve 147 (FIG. 3) and thus clamp down the entire handle and shaft assembly.

The blood pump 10 also includes a drive piston mechanism having a horizontal drive plate which has the same dimensions as the box 50 and fits inside the box 50 with short vertical end walls 166, 168 and side walls 170, 172 bearing against the inner surface of side walls 54 and 56 and end walls 51 and 52 of box 50. The inner surfaces of walls 54 and 56 also carry stops 176 against which the horizontal plate 164 bears. At about the center of the plate 164, a vertical tube 70 rises and includes at its upper end an inwardly extending annular lip 73 which engages the upper surface of the nut 150. An inner cylinder 179 is secured inside the vertical tube 70 and engages the lower surface of the nut 150. The nut 150 is thus firmly secured in the tube 70 and can move the drive piston up and down when the handle 100 is turned. Springs 160 are disposed between the bottom wall of the box 50 and the lower surface of the drive plate 164.

A rigid hanger 58 is secured to the bottom wall 52 of box 50 at any suitable location.

If desired, means for heating a blood bag is provided and, in one form, this heating means comprises a plate 173 carrying heating wires (not shown) and disposed adjacent to the outer surface of bottom wall 52 of box 50. The heater plate is secured in place in any suitable fashion.

Figure 4:
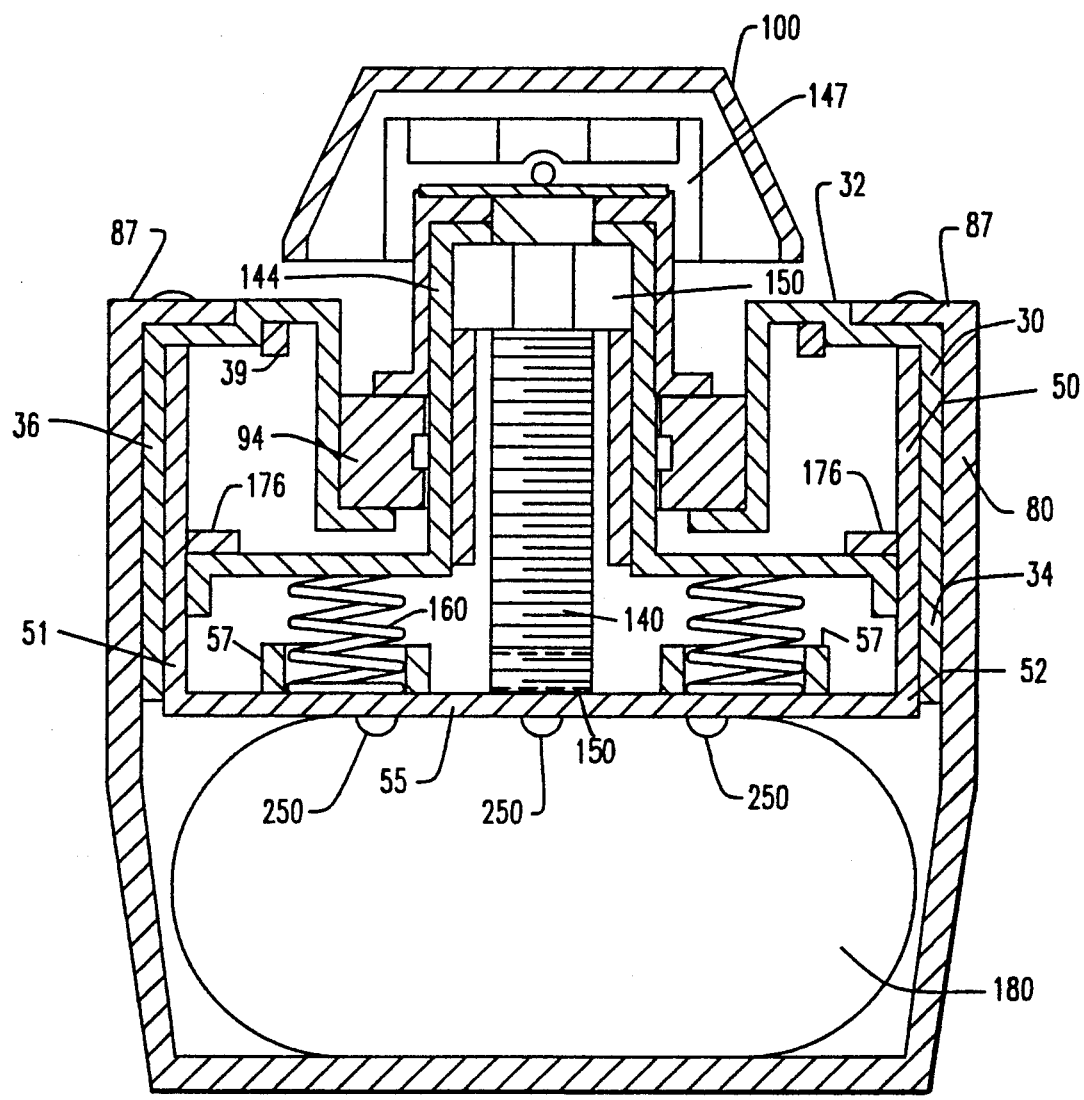
FIG. 4 is a view similar to that of FIG. 2 showing the apparatus of the invention in use.

In operation of the apparatus 10, the handle 100 is rotated to raise the nut 150 and to raise the lower box 50 due to the fact that the drive plate 164 bears against the stops 176. A space is thus provided (FIG. 4) between the bottom wall of the box 50 and the bottom wall of the wrapping sheet 80 and a blood bag 180 having dispensing tubes (not shown) is inserted in this space. Next, the handle 100 is rotated to drive the nut 150 and plate 164 down, thereby compressing the springs 160 and causing the springs to press the lower wall of box 50 against the blood bag and to cause blood to flow therefrom. This flow is caused merely by the pressure of the springs and with no manipulation of the handle 100 by an operator. If additional pressure is needed at some time during the removal of blood from the bag, the handle can be rotated to compress the springs again and provide the additional feeding pressure required.

If desired, a stop may be provided on the inner wall 51 of the lower box 50 to limit the downward movement of the drive piston.

Figure 5:
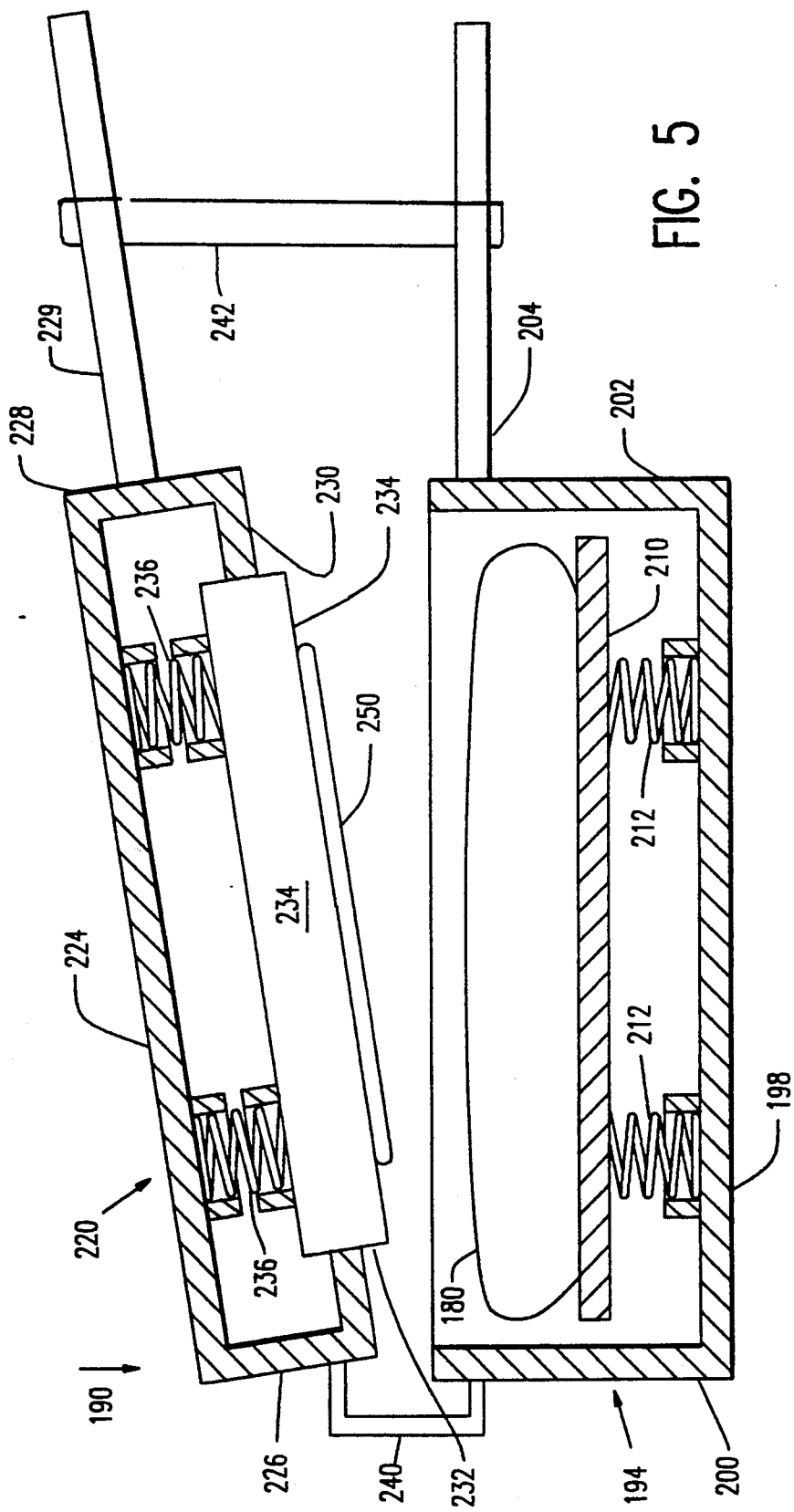
FIG. 5 is a side sectional view of a modification of the invention.

A modification of the invention, apparatus 190, shown in FIG. 5 is like a conventional nutcracker and includes a lower U-shaped box member 194 open at the top and including a bottom wall 198, end walls 200, 202 and side walls (not shown). A handle 204 is secured to the end wall 202. A movable horizontal plate 210 is loosely disposed within the member and is secured to the bottom wall 198 by means of a plurality of springs 212 secured to the lower surface thereof.

The apparatus of FIG. 5 also includes an upper U-shaped box member 220 having a top wall 224, end walls 226, 228 and side walls (not shown) a bottom wall having a large opening 232 in which is loosely mounted a horizontal plate 234. The plate 234 is secured to the top wall by means of springs 236 secured to the upper surface thereof. A handle 229 is secured to the end wall 228 of upper box member 220 so that it overlies and is in operative relation with handle 204.

The upper and lower members 220 and 194 are coupled together along the walls 200 and 226 by means of a suitable joint represented by numeral 240 so that they can be spread apart and brought together about the joint 240 as a pivot point. Any suitable pivoting coupling arrangement may be used.

In operation of the apparatus 190 of FIG. 5, a blood bag 180 is placed on the plate 212 and the upper member 220 is positioned over the blood bag with the plate 234 in contact with the blood bag and exerting pressure thereon by means of the compressed springs 212 and 236. The handles 204 and 229 are held together by a suitable clamp 242 and as pressure is applied, blood flows out of the blood bag through a suitable tube (not shown).

If desired, the plate 234 may be secured to walls 230 and held securely in place. In this case, pressure would be applied to the blood bag by means of only springs 212.

Figure 6:
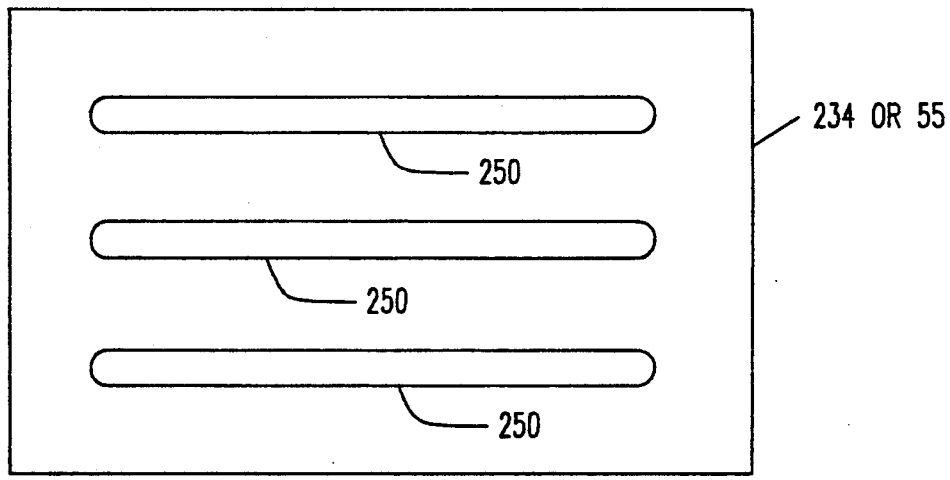
FIG. 6 is a bottom view of a portion of either embodiment of the invention illustrating a modification thereof.

In both devices 10 and 190, the lower surface of plate 55 in device 10 and the lower surface of plate 234 in device 190 are provided with a suitable number of ribs 250 which extend a convenient distance, preferably longitudinally, along the outer surfaces thereof as illustrated in FIG. 6. The ribs do not extend to the ends of the plates so that blood flow from a blood bag is not impeded. The ribs 250 limit the downward movement of these plates so that a blood bag is not completely crushed thereby. This prevents crushing of blood cells but permits the proper outflow of blood around the ends of the ribs.

What is claimed is:

1. Fluid dispensing apparatus comprising
a first receptacle,
a second receptacle,
said first receptacle being adapted to be moved with respect to said second receptacle to thereby provide a space beneath it for receiving a deformable container of a fluid to be fed therefrom,
spring means engaging said first receptacle for urging said first receptacle against said deformable container and thereby forcing fluid therefrom,
first means associated with said first receptacle and movable with respect to said first receptacle, said first means engaging said spring means, and
second means coupled to said first means and operable to move said first means to compress said spring means whereby said firs receptacle is forced against said container and forces fluid therefrom.

2. The apparatus defined in claim 1 and including a drive shaft and said first means includes a coupling between said drive shaft and said first receptacle whereby said drive shaft can slide said first receptacle into said second receptacle and it can also drive said first receptacle out of said second receptacle into pressure contact with said container.

3. The apparatus defined in claim 2 wherein said first means includes a vertical tube having an upper end and a lower end with said upper end engaging said drive shaft and said lower end being secured to a horizontal plate, said horizontal plate being movable with respect to said first receptacle, and said spring means comprises a plurality of springs disposed between said horizontal plate and said first receptacle.

4. The apparatus defined in claim 3 and including means on said first receptacle, said horizontal plate being positioned to engage said means on said first receptacle whereby said horizontal plate can slide said first receptacle into said second receptacle.

5. The apparatus defined in claim 1 wherein said first and second receptacles are pivotally coupled together so that they can be pivoted with respect to each other to bring one into operative relation with the other.

6. The apparatus defined in claim 1 wherein said first means is a horizontal plate adapted to support a deformable fluid container,
a horizontal plate in said second receptacle positioned to overlay said horizontal plate in said first receptacle and to apply pressure to said container.

7. The apparatus defined in claim 1 wherein said first receptacle includes a bottom wall having an outer surface which contacts a deformable container and a plurality of ribs on said outer surface of said first receptacle for limiting the movement of said first receptacle against said deformable container.

8. The apparatus defined in claim 1 wherein said second means can move said first means in a first direction to form said space and in a second direction in which said first means compresses said spring means.

9. Fluid dispensing apparatus comprising
a housing,
a first receptacle in said housing,
a second receptacle in said housing,
said first and second receptacles being movable with respect to each other to provide a space between said first receptacle and a portion of said housing for receiving a deformable container of a fluid to be fed therefrom,
first means associated with said first receptacle and movable with respect to said first receptacle, and
spring means disposed between said first means and a portion of said first receptacle,
said first means being movable with respect to said first receptacle in a first direction to form said space and in a second direction to compress said spring means whereby said first receptacle is forced against said container and forces fluid therefrom.

10. Fluid dispensing apparatus comprising
a housing,
a first lower receptacle in said housing,
a second upper receptacle in said housing, said first receptacle being movable into said second receptacle to provide a space between said first receptacle and a portion of said housing for receiving a deformable container of a fluid to be fed therefrom, a screw mechanism mounted in said housing and extending into said housing and having a lower end, a horizontal wall within said first receptacle and engaging a portion of said first receptacle and movable with respect to said first receptacle, said horizontal wall including a portion which engages said lower end of said screw mechanism whereby said screw mechanism can raise and lower said horizontal wall, and a plurality of springs disposed between said horizontal wall and a portion of said first receptacle, and said horizontal wall being movable in a first direction to form said space and in a second direction to compress said springs whereby said first receptacle is forced against said container and forces fluid therefrom.

11. Fluid dispensing apparatus comprising
a first receptacle,
a second receptacle,
said first and second receptacles being coupled together so that they can move with respect to each other,
first means in said first receptacle for supporting a deformable container containing a fluid to be dispensed,
second means in said second receptacle positioned to bear against said container to apply pressure to dispense fluid therefrom,
first spring means beneath said first means, and
second spring means engaging said second means to urge it against said container to assist the fluid dispensing operation.

12. The apparatus defined in claim 11 and including a first operating handle secured to said first receptacle and a second operating handle secured to said second receptacle.

13. The apparatus defined in claim 11 wherein said first means is a horizontal support plate,
said second means is a horizontal plate, and
a plurality of guide strips on the lower surface of said second means which engages said container.

* * * * *